United States Patent [19]

Kaplan et al.

[11] 4,188,335
[45] Feb. 12, 1980

[54] NOVEL SOLVENTS FOR THE CATALYTIC PROCESS FOR PRODUCING POLYHYDRIC ALCOHOLS

[75] Inventors: Leonard Kaplan, Charleston, W. Va.; Frank A. Cotton, Bryan, Tex.

[73] Assignee: Union Carbide Corporation, New York, N.Y.

[21] Appl. No.: 890,969

[22] Filed: Mar. 28, 1978

[51] Int. Cl.$^2$ .................................................. C07C 27/06
[52] U.S. Cl. ................................ 260/449 L; 260/449.5
[58] Field of Search ........................ 260/449 R, 449 L

[56] References Cited

U.S. PATENT DOCUMENTS

| 3,944,588 | 3/1976 | Kaplan | 260/449 R |
| 3,952,039 | 4/1976 | Walker et al. | 260/449 R |
| 3,968,136 | 7/1976 | Walker et al. | 260/449 R |

OTHER PUBLICATIONS

Knipe, J. of Chem. Ed., 53 (1976), pp. 618–622.

Primary Examiner—Howard T. Mars
Attorney, Agent, or Firm—Marylin Klosty

[57] ABSTRACT

This invention relates to the manufacture of polyhydric alcohol(s) by the reaction of synthesis gas in the presence of a rhodium carbonyl complex dissolved in a substituted gamma-butyrolactone solvent.

13 Claims, No Drawings

NOVEL SOLVENTS FOR THE CATALYTIC PROCESS FOR PRODUCING POLYHYDRIC ALCOHOLS

This invention relates to an improved process for the manufacture of polyhydric alcohols, in particular alkane polyols, as well as a variety of other chemicals, in particular methanol, from synthesis gas, i.e., a mixture of carbon monoxide and hydrogen.

Specifically, this invention is directed to an improved process of making alkane diols, triols, tetraols, etc., containing 2, 3, 4 or more carbon atoms. A key product of the process of this invention is ethylene glycol. By-products of this invention are the lesser valuable, but nonetheless valuable, monohydric alkanols such as methanol, and ethanol. The products of the process of this invention contain carbon, hydrogen and oxygen.

There are described in U.S. Pat. No. 3,833,634 issued Sept. 3, 1974, and U.S. Pat. No. 3,957,857, issued May 18, 1976, processes for reacting hydrogen and oxides of carbon in the presence of rhodium carbonyl complex catalysts. The conditions employed in those processes involve reacting a mixture of an oxide of carbon and hydrogen with a catalytic amount of rhodium in a complex combination with carbon monoxide, at a temperature of between about 100° C. and about 375° C. and a pressure of between about 500 p.s.i.a. and about 50,000 p.s.i.a. In addition to the aforementioned U.S. Patents, the following U.S. Patents and U.S. Patent applications amplify the development of the process for making alkane polyols from mixtures of hydrogen and oxides of carbon:

U.S. Pat. No. 3,878,292—Patented Apr. 15, 1975
U.S. Pat. No. 3,878,290—Patented Apr. 15, 1975
U.S. Pat. No. 3,878,214—Patented Apr. 15, 1975
U.S. Pat. No. 3,886,364—Patented May 27, 1975
U.S. Pat. No. 3,940,432—Patented Feb. 24, 1976
U.S. Pat. No. 3,929,969—Patented Dec. 30, 1976
U.S. Pat. No. 3,952,039—Patented Apr. 20, 1976
U.S. Pat. No. 3,948,965—Patented Apr. 6, 1976
U.S. Pat. No. 3,944,588—Patented Mar. 16, 1976
U.S. Pat. No. 3,957,857—Patented May 18, 1976
U.S. Pat. No. 3,974,259—Patented Aug. 10, 1976 (formerly U.S. Ser. No. 455,380, filed Mar. 27, 1974)
U.S. Pat. No. 3,989,799—Patented Nov. 2, 1976 (formerly U.S. Ser. No. 455,379, filed Mar. 27, 1974)
U.S. Pat. No. 4,013,700—Patented Mar. 22, 1977 (formerly U.S. Ser. No. 526,942, filed Nov. 25, 1974)
U.S. Ser. No. 488,139—Filed July 12, 1974 (now abandoned)
U.S. Ser. No. 506,862—Filed Sept. 17, 1974 (now abandoned)
U.S. Pat. No. 4,001,289—Patented Jan. 4, 1977 (formerly U.S. Ser. No. 506,864, filed Sept. 17, 1974)
U.S. Ser. No. 506,865—Filed Sept. 17, 1974 (now abandoned)
U.S. Ser. No. 615,093—Filed Sept. 19, 1975
U.S. Ser. No. 537,885—Filed Jan. 2, 1975 (now abandoned)
U.S. Ser. No. 618,023—Filed Sept. 30, 1975 (now abandoned)
U.S. Ser. No. 618,061—Filed Sept. 30, 1975 (now abandoned)
U.S. Ser. No. 618,021—Filed Sept. 30, 1975
U.S. Ser. No. 727,646—Filed Sept. 29, 1976 (now abandoned)
U.S. Ser. No. 782,986—Filed Mar. 30, 1977 (now U.S. Pat. No. 4,111,975, patented Sept. 5, 1978).

Also, U.S. Pat. No. 3,968,136 patented July 6, 1976 describes a process for producing alkane polyols from mixtures of hydrogen and oxides of carbon in the presence of a rhodium carbonyl complex dissolved in a solvent selected from gamma-butyrolactone and delta-valerolactone at a temperature of between about 100° C. and about 375° C. and a pressure between about 1000 and about 50,000 psig.

The gamma-butyrolactone and delta-valerolactone solvents as described in U.S. Pat. No. 3,968,136 are good solvents for the production of alkane polyols from synthesis gas. However, under the reaction conditions which produce the alkane polyols, it is postulated that the aforedescribed lactone solvents react with the hydroxylic compounds present therein. This is based on the fact that gamma-butyrolactone reacts with water and alcohols. The equilibrium constant, K, for the reaction of gamma-butyrolactone with water and also, the rate constant, k, for saponification of gamma-butyrolactone have been measured.

The equilibrium constant, K, measured at 25° C. is 35 $M^{-1}$ for the following reaction:

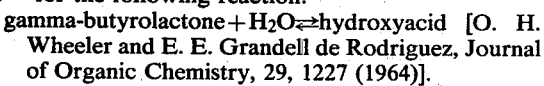

[O. H. Wheeler and E. E. Grandell de Rodriguez, Journal of Organic Chemistry, 29, 1227 (1964)].

The rate constant, k, for the saponification of gamma-butyrolactone in a solution of 92 percent ethanol at 25° C. is 0.047 $M^{-1}Sec^{-1}$ [O. H. Wheeler and D. S. Gamble, Journal of Organic Chemistry, 26, 3221 (1961)].

Thus, if the gamma-butyrolactone solvent reacts with the hydroxylic compounds produced in the reaction of synthesis gas in the presence of rhodium carbonyl complexes, the gamma-butyrolactone solvent must be continually provided to the reaction to make up for this solvent loss.

The equilibrium constant, K, and the rate constant, k, for a substituted-gamma-butyrolactone of the present invention, i.e., 2, 2-dimethyl-gamma-butyrolactone, are <1.0 and 0.013, respectively. These values indicate that the substituted-gamma-butyrolactone would be less reactive with hydroxylic compounds.

Also, it has been discovered that when the substituted-gamma-butyrolactone solvent of the present invention is used with a co-solvent, there is an improvement, both in the rate of production of alkane diols and retention of rhodium in solution. The retention of rhodium in solution is quite important since rhodium is an extremely expensive metal; it currently has a dealer's price of about $525 per troy ounce, so that it is particularly desirable to minimize any loss of such rhodium values during the course of the reaction. Additionally, when the substituted-gamma-butyrolactone solvents of the present invention are used with a co-solvent, their stability under reaction conditions is much greater than that of gamma-butyrolactone solvent.

The process of the present invention involves the production of polyhydric alcohol(s) by reacting in a solvent comprising substituted gamma-butyrolactone at a pressure between about 1000 psig and 50,000 psig and a temperature between about 100° C. and 375° C., oxides of carbon and hydrogen in the presence of a rhodium carbonyl complex.

The substituted-gamma-butyrolactone solvents of the present invention are prepared according to the following procedure, which illustrates the preparation of 2,2-dimethyl-gamma-butyrolactone:

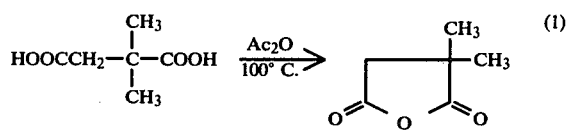

(as described by H. E. Baumgarten and D. C. Gleason, Journal of Organic Chemistry, 16, 1658, 1951)

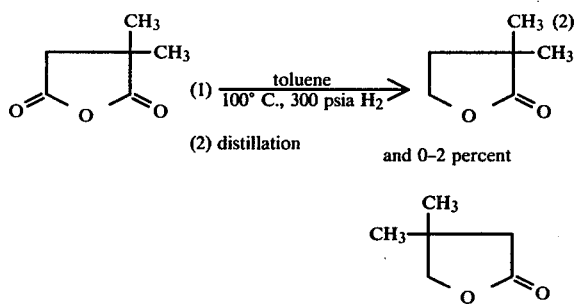

and 0-2 percent

Reaction (2) is catalyzed by RuCl$_2$ (triphenylphosphine)$_3$. (Reaction (2) is described by R. Morand & M. Kayser, Chemical Communications, p. 314 1976.)

The substituted gamma butyrolactone solvents of the present invention are characterized by the following formula:

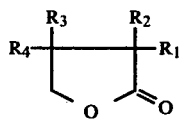

wherein R$_1$ through R$_4$ is at least one of hydrogen, straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo [2.2.1] heptyl, and the like; or an aryl, alkaryl, or aralkyl group such as phenyl, naphthyl, xylyl, tolyl, benzyl, beta-phenylethyl and the like; an ether of the formula (O—R°) wherein R° may be aryl or lower alkyl having from 1 to 12 carbon atoms, preferably 1 to 4 carbon atoms in the alkyl chain; and alkylene or polyalkylene ether of the formula —OC$_n$H$_{2nx}$OR°° wherein n has an average value of from 1 to about 4, x has an average value of from 1 to about 150, preferably 1 to about 20, most preferably 1 to about 4, and R°° may be alkyl having from 1 to 6 carbon atoms in the alkyl chain, such as poly(oxyethylene), poly(oxypropylene), poly(oxyethylene-oxypropylene), alkyl ethers of alkylene and polyalkylene glycols;

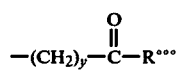

wherein y may have any value between 0 and 12 and R°°° may be a lower alkyl group having from 1 to 12 carbon atoms, preferably from 1 to 4 carbon atoms, or aryl; provided that one of R$_1$ or R$_2$ is other than hydrogen.

Preferably, the substituted-gamma-butyrolactone solvent used in the practice of the present invention is 2,2-di(alkyl) substituted-gamma-butyrolactone, wherein the alkyl group contains 1 to 12 carbon atoms, and preferably 1 to 6 carbon atoms. The most preferred 2,2-di(alkyl)-gamma-butyrolactone solvent is 2,2-dimethyl-gamma-butyrolactone.

Illustrative co-solvents which are generally suitable for use with the substituted gamma-butyrolactone solvents herein include, for example, ethers such as tetrahydrofuran, tetrahydropyran, diethyl ether, 1,2-dimethoxybenzene, 1,2-diethoxybenzene, the dialkyl ethers of ethylene glycol, of propylene glycol, of butylene glycol, of diethylene glycol, of dipropylene glycol, of triethylene glycol, of tetraethylene glycol, of dibutylene glycol, of oxyethylene propylene glycol, etc; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; substituted and unsubstituted tetrahydrothiophene-1,1-dioxides (sulfolanes) as disclosed in U.S. Ser. No. application 537,885, filed on Jan. 2, 1975, the disclosure at pages 6 and 7 of the specification of which is incorporated herein by reference; butyrolactone as described in U.S. Pat. No. 3,968,136, which is incorporated herein by reference.

Also, the crown ethers are suitable co-solvents herein, particularly those as described in U.S. patent application Ser. No. 832,384 filed Sept. 13, 1977, now U.S. Pat. No. 4,162,261, which application is incorporated herein by reference. The crown ethers described therein contain at least four oxygen heteroatoms each separated from the other by at least two aliphatic carbon atoms in series. These crown ethers include [18]-crown-6 and [15]-crown-5.

The preferred co-solvents include tetraglyme and [18]-crown-6

This ratio of the substituted-gamma-butyrolactone solvent to co-solvent, hereafter referred to as the "solvent ratio," may range from 1 to 20 to 50 to 1, determined on a volume basis. However, it is to be emphasized that in any reaction system, such factors as the ratio of carbon monoxide to hydrogen, temperature and pressure selected, concentrations of added components such as catalysts and promoters, the nature of the promoter, play a role in determining what solvent ratio is most effective. When selecting the appropriate solvent ratio one will be required to explore in a number of experiments in a given reaction system, a number of ratios such that the optimum solvent ratios can be determined.

The rhodium carbonyl complex catalysts suitable for use herein may be in the form of rhodium carbonyl clusters. P. Chini, in a review article entitled "The Closed Metal Carbonyl Clusters" published in Review (1968), Inorganica Chimica Acta, pages 30–50, states that a metal cluster compound is "a finite group of metal atoms which are held together entirely, mainly, or at least to a significant extent by bonds directly between the metal atoms even though some non-metal atoms may be associated intimately with the cluster." The rhodium carbonyl clusters contain rhodium bonded to rhodium or rhodium bonded to another metal, such as cobalt and/or iridium. The preferred rhodium carbonyl cluster compounds are those which contain rhodium-rhodium bonds. These compounds desirably contain carbon and oxygen in the form of carbonyl (—CO), in which the carbonyl may be "terminal", "edge-bridging", and/or "face-bridging". They may also contain hydrogen and carbon in forms other than carbonyl. The structure of two distinct rhodium carbonyl clusters having the formula $Rh_6(CO)_{16}$ and $Rh_{12}(CO)_{30}{}^{2-}$, and both suitable for use in this invention are shown, for example, in U.S. Pat. No. 3,957,857.

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chimica Acta, 3:2 pp299–302, June (1969). Of particular analytical utility in the present invention is the use of infrared spectroscopy which allows for characterization of the particular rhodium carbonyl complex present during the operation of the process of the present invention.

A number of nitrogen and/or oxygen-containing bases may be used in the process of the present invention. For the purposes of this invention, the bases can be considered to promote the activity of the rhodium catalysts.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino(—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the

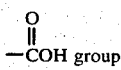

and the "oxy" oxygen in the

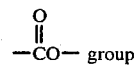

that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di-, tri-, tetraamines, etc.) and those compounds in which the Lewis base nitrogen forms part of a ring structure as in pyridine, quinoline, pyrimidine morpholine, hexamethylenetetraamine, and the like. In addition any compounds capable of yielding an amino nitrogen under the reaction conditions of the present invention are promoters, as in the case of an amide, such as formamide, cyanamide, and urea, or an oxime. Further illustrative of Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino) pyridine;

quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'dipyridyl, methyl-substituted 2,2-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo [2.2.2]octane, purine and the like.

Also included herein are the use of dimorpholine compounds characterized by the formula:

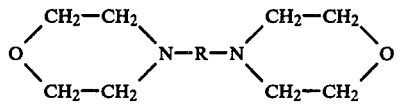

wherein R is divalent alkylene of 1 to about 30 carbon atoms and 1,4-phenylene.

The base provided to the reaction mixture is present in an amount which is equal to or greater than that amount, determined from the bases basicity, which achieves the optimum rate of formation of said alkane polyol at said correlated catalyst concentration, temperature and pressure of such reaction mixture.

The concentration of the base will typically be within about 0.001 to about 10 molar. Obviously this range is definitive of the potential scatter of concentrations predicated on the varieties of the basicities of the bases available.

Under reaction conditions the base is preferably used in amounts from about 0.02 to about 40 equivalents of base, most preferably from about 0.1 to about 20 equivalents base, for every atom of rhodium in the reaction mixture. The number of equivalents of base is equal to the number of molecules of base times the number of nitrogen atoms in each molecule.

In practicing the method of the present invention, the synthesis of the desired alkane diols and derivatives thereof, by the reaction of hydrogen with an oxide of carbon is suitably conducted under operative conditions, as heretofore described, which give reasonable reaction rates and/or conversions.

The process is suitably effected over a wide superatmospheric pressure range of from about 800 psia to about 50,000 psia. Pressures as high as 50,000 psia, and higher can be employed but with no apparent advantages attendant thereto which offset the unattractive plant investment outlay required for such high pressure equipment. Therefore, the upper pressure limitation is desirably approximately 16,000 psia. Effecting the present process below about 16,000 psia, especially below about 13,000 psia, and preferably at pressures below about 8000 psia, results in cost advantages which are associated with low pressure equipment requirements. In attempting to foresee a commercial operation of this process, pressures between about 4,000 psia and 16,000 psia appear to represent most realistic values.

In a preferred embodiment of the present invention the pressures referred to above represent the total pressures of hydrogen and oxides of carbon in the reactor.

The process of this invention can also be carried out by providing salts in the homogeneous liquid phase reaction mixture. Suitable salts include any organic or inorganic salt which does not adversely affect the production of polyhydric alcohols. Experimental work suggest that any salt is beneficial as either a copromoter and/or in aiding in maintaining rhodium in solution during the reaction. Illustrative of the salts useful in the practice of the present invention are the ammonium salts and the salts of the metals of Group I and Group II of the Periodic Table (Handbook of Chemistry and Physics - 50th Edition) for instance the halide, hydroxide, alkoxide, phenoxide and carboxylate salts such as sodium fluoride, cesium fluoride, cesium pyridinolate, cesium formate, cesium acetate, cesium benzoate, cesium p-methylsulfonylbenzoate $(CH_3SO_2C_6H_4COO)Cs$, rubidium acetate, magnesium acetate, strontium acetate, ammonium formate, ammonium benzoate and the like. Preferred are the cesium, rubidium, potassium, and ammonium salts.

Also useful in the practice of the present invention are organic salts of the following formula:

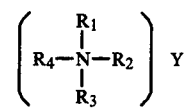

quaternary ammonium salts

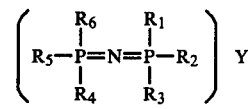

bis(triorgano phosphine)iminium salts wherein $R_1$ through $R_6$ in formulas (II) and (III) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1]heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $(C_nH_{2n}O)_x$—OR wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas I and II above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas I and II, above, is a carboxylate, most preferably formate, acetate and benzoate.

A suitable method for preparing the bis(triorganophosphine) iminium salts is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

In addition, the anion of the above salt may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; $[Rh_{12}(CO)_{30}]^{2-}$; $Rh_{13}(CO)_{24}H_3{}^{-2}$; and $Rh_{13}(CO)_{24}H_2{}^{-3}$.

Under reaction conditions where a salt is employed the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

The temperature which may be employed can vary over a wide range of elevated temperatures. In general, the process can be conducted at a temperature in the range of from about 100° C. and upwards to approximately 375° C., and higher. Temperatures outside this stated range are not excluded from the scope of the invention. At the lower end of the temperature range, and lower, the rate of reaction to desired product becomes markedly slow. At the upper temperature range, and beyond, signs of some catalyst instability are noted. Notwithstanding this factor, reaction continues and alkane polyols and/or their derivatives are produced. Additionally, one should take notice of the equilibrium reaction for forming ethylene glycol

$$2CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher pressures, however, do not represent preferred embodiments of the invention in view of the high investment costs associated with erecting chemical plants which utilize high pressure utilities and the necessity of fabricating equipment capable of withstanding such enormous pressures. Suitable temperatures are between about 150° C. to about 350° C., and desirably from about 210° C. to about 320° C.

The process is effected for a period of time sufficient to produce the alkane polyols and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressures exerted by its components, the concentration and choice of diluent, and other factors. The synthesis of the desired product(s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is understood, however, that molar ratios outside the aforesaid broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction.

Means to introduce and/or adjust the reactants, either intermittently or continuously, into the reaction zone during the course of the reaction can be conveniently utilized in the novel process especially to maintain the desired molar ratios of and the partial pressures exerted by the reactants.

The operative conditions can be adjusted to optimize the conversion of the desired product and/or the economics of the process. In a continuous process, for instance, when it is preferred to operate at relatively low conversions, it is generally desirable to recirculate unreacted synthesis gas with/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and intermittently added to the recycle stream or directly to the reaction zone.

The active forms of the rhodium carbonyl clusters may be prepared by various techniques. They can be preformed and then introduced into the reaction zone or they can be formed in situ.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Pat. No. 3,957,857 the disclosure of which is incorporated herein by reference.

A particularly desirable infrared cell construction is described in U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction.

The following examples are merely illustrative and are not presented as a definition of the limits of the invention:

EXAMPLES 1 TO 21

A 150 ml. capacity stainless steel reactor capable of withstanding pressures up to 7,000 atmospheres was charged with a premix of 75 cubic centimeters (cc) of the indicated solvent(s), the indicated amount (mmoles) of rhodium dicarbonylacetylacetonate, and promoter(s). The reactor was sealed and charged with a gaseous mixture, containing equal molar amounts of carbon monoxide and hydrogen to a pressure in pounds per square inch (psig) as set forth in the Table. Heat was applied to the reactor and its contents; when the temperature of the mixture inside the reactor reached the temperature (in °C.) as set forth in the Table and as measured by a suitably placed thermocouple, an additional adjustment of carbon monoxide and hydrogen ($H_2$:CO)=1:1 mole ratio was made to bring the pressure back to the pressure reported in the Table. Additional carbon monoxide and hydrogen was added whenever the pressure inside the reactor dropped below about 7500 psig. With these added repressurizations, the pressure (psig±400 psig) inside the reactor was maintained over the entire reaction period.

After the reaction period, the vessel and its contents were cooled to room temperature, the excess gas vented and the reaction product mixture was removed. Analysis of the reaction product mixture was made by gas chromatographic analysis using a Hewlett Packard FM$^{TM}$ model 810 Research Chromatograph.

Rhodium recovery was determined by atomic absorption analysis of the contents of the reactor after the venting of the unreacted gases at the end of the reaction.

An atomic absorption analysis for rhodium was run on the reactor's contents. The rhodium recovery values recited below are the percent rhodium based on the total rhodium charged to the reactor that is soluble or suspended in the reaction mixture after the specified reaction time. The results are set forth in the Table.

Also, the percent decrease of the quantity of 2,2-dimethyl-gamma-butyrolactone and gamma-butyrolactone, each relative to tetraglyme, is set forth in the Table.

TABLE

| Ex. | Solvent[a] (Volume/Volume) | Pressure (psig) | Temp. (°C.) | Salt[b] (mmoles) | Amine (mmoles) | Rh(CO)$_2$acac[c] (mmoles) | Rate CH$_3$OH | (Mole Liter$^{-1}$ Hour$^{-1}$) HOCH$_2$CH$_2$OH | Rh Recovery | % Decrease of the ratio of the butyrolactone to tetraglyme |
|---|---|---|---|---|---|---|---|---|---|---|
| 1 | TG | 8000 | 240 | PhCO$_2$Cs (0.65) | — | 3 | 0.45 | 0.31 | 27 | |
| 2 | γ-B | 8000 | 240 | " | — | 3 | 0.59 | 0.57 | 85 | |
| 3 | DM-B | 8000 | 240 | " | — | 3 | 0.59 | 0.65 | 81 | |
| 4 | TG | 12,500 | 250 | PhCO$_2$Cs (0.75) | Pyridine (1.25) | 3 | 3.2 | 3.0 | 79 | |
| 5 | TG/γ-B (57/18) | 12,500 | 250 | " | " | 3 | 4.8 | 3.3 | 102 | |
| 6 | TG/DM-B (57/18) | 12,500 | 250 | " | " | 3 | 3.3 | 3.3 | 102 | |
| 7 | TG | 15,000 | 260 | " | " | 3 | 9.3 | 5.7 | 90 | |
| 8 | TG/γ-B (57/18) | 15,000 | 260 | " | " | 3 | ~7.3,~4.9 | 8.5,7.8 | 103,102 | 7.6 in 31 min |
| 9 | TG/DM-B (57/18) | 15,000 | 260 | " | " | 3 | ~3.9 | 8.0 | 107 | 3.9 in 31 min |
| 10 | CR | 15,000 | 270 | PhCO$_2$Cs (0.50) | — | 1.5 | 6.4,7.4 | 6.7,7.5 | 87,87 | |
| 11 | CR/γ-B (57/18) | 15,000 | 270 | " | — | 1.5 | 8.0 | 10.4 | 110 | |
| 12 | CR/DM-B (57/18) | 15,000 | 270 | " | — | 1.5 | ~6.3 | 9.5 | 94 | |
| 13 | TG | 8,000 | 240 | PhCO$_2$Cs (0.65) | — | 3.0 | 0.45 | 0.31 | 27 | |
| 14 | TG/γ-B (48/27) | 8,000 | 240 | " | — | 3.0 | ~0.54 | 0.66 | 89 | 1.5 in 4 hrs. |
| 15 | TG/DM-B (48/27) | 8,000 | 240 | " | — | 3.0 | ~0.60 | 0.68 | 88 | 0.2 in 4 hrs. |
| 16 | TG | 8000 | 240 | PhCO$_2$Cs (0.325) | — | 1.5 | 0.40 | 0.29 | 9 | |
| 17 | TG/γ-B (48/27) | 8000 | 240 | " | — | 1.5 | 0.41 | 0.53 | 50 | 7.4 in 12 hr. |
| 18 | TG/DM-B (48/27) | 8000 | 240 | " | — | 1.5 | 0.42 | 0.41 | 45 | 1.4 in 12 hr. |
| 19 | TG | 12,500 | 250 | PhCO$_2$Cs | Pyridine | 0.5 | 0.62 | 0.72 | 8 | |

TABLE-continued

| Ex. | Solvent[a] (Volume/ Volume) | Pressure (psig) | Temp. (°C.) | Salt[b] (mmoles) | Amine (mmoles) | Rh(CO)$_2$acac[c] (mmoles) | Rate CH$_3$OH | (Mole Liter$^{-1}$ Hour$^{-1}$) HOCH$_2$CH$_2$OH | Rh Recovery | % Decrease of the ratio of the butyrolactone to tetraglyme |
|---|---|---|---|---|---|---|---|---|---|---|
| 20 | TG/γ-B (57/18) | 12,500 | 250 | (0.13) " | (0.4) " | 0.5 | 1.3 | 2.9 | 72 | 17 in 10.3 hr. |
| 21 | TG/DM-B (57/18) | 12,500 | 250 | " | " | 0.5 | 1.6 | 3.1 | 62 | 4.6 in 10.3 hr. |

[a]TG:tetraglyme; γB=γ-butyrolactone; DM-B=dimethyl-gamma-butyrolactone; CR=[18]-crown-6
[b]PhCO$_2$Cs: cesium benzoate
[c]Rh(CO)$_2$acac: rhodium dicarbonylacetylacetonate
[d]Scaled proportionately to 6mmoles of Rh(CO)$_2$ acac

What is claimed is:

1. The process for producing polyhydric alcohol(s) which comprises reacting hydrogen and oxides of carbon in a solvent comprising a 2,2-di(alkyl)-gamma-butyrolactone wherein the alkyl groups have from 1 to 12 carbon atoms, in the presence of a rhodium carbonyl complex at a temperature of between about 100° C. and 375° C. and a pressure of between about 1000 psia. and 50,000 psia. to produce said polyhydric alcohol(s).

2. The process of claim 1 wherein the temperature of the reaction is between about 150° C. and 320° C.

3. The process of claim 2 wherein the temperature of the reaction is between about 190° C. and 290° C.

4. The process of claim 1 wherein the pressure of the reaction is between about 1000 psia and 25,000 psia.

5. The process of claim 4 wherein the pressure of the reaction is between about 1000 psia and 17,000 psia.

6. The process of claim 1 wherein the 2,2-di-(alkyl)-gamma-butyrolactone is 2,2-dimethyl-gamma-butyrolactone.

7. The process of claim 1 wherein the solvent is employed with a co-solvent.

8. The process of claim 7 wherein the cosolvent is sulfolane.

9. The process of claim 7 wherein the cosolvent is tetraglyme.

10. The process of claim 7 wherein the cosolvent is a crown ether.

11. The process of claim 10 wherein the crown ether is [18]-crown-6.

12. The process of claim 1 wherein the alkane polyol is ethylene glycol.

13. The process of claim 1 wherein the principal products recovered are ethylene glycol and methanol.

UNITED STATES PATENT AND TRADEMARK OFFICE
CERTIFICATE OF CORRECTION

PATENT NO. : 4,188,335
DATED : February 12, 1980
INVENTOR(S) : Leonard Kaplan et al.

It is certified that error appears in the above—identified patent and that said Letters Patent is hereby corrected as shown below:

Column 3, line 53, "$-OC_nH_{2nx}OR^{\circ\circ}$" should read -- $-(OC_nH_{2n})_{\overline{x}} OR^{\circ\circ}$ --.

Column 4, line 42, "hereafter" should read -- hereinafter --.

Signed and Sealed this

*Fourteenth* Day of *July 1981*

[SEAL]

*Attest:*

*Attesting Officer*

GERALD J. MOSSINGHOFF

*Commissioner of Patents and Trademarks*